United States Patent
Dirk et al.

(10) Patent No.: US 9,555,583 B1
(45) Date of Patent: Jan. 31, 2017

(54) FABRICATION OF NEURAL INTERFACES USING 3D PROJECTION MICRO-STEREOLITHOGRAPHY

(71) Applicants: Sandia Corporation, Albuquerque, NM (US); STC.UNM, Albuquerque, NM (US); Board of Regents, The University of Texas System, Austin, TX (US)

(72) Inventors: Shawn M. Dirk, Albuquerque, NM (US); Stephen Buerger, Albuquerque, NM (US); Kirsten Nicole Cicotte, Salem, NY (US); Elizabeth L. Dirk, Albuquerque, NM (US); Greg Reece, Sugar Land, TX (US); Patrick Lin, Bellaire, TX (US)

(73) Assignees: Sandia Corporation, Albuquerque, NM (US); STC.UNM, Albuquerque, NM (US)

( * ) Notice: Subject to any disclaimer, the term of this patent is extended or adjusted under 35 U.S.C. 154(b) by 541 days.

(21) Appl. No.: 14/085,671

(22) Filed: Nov. 20, 2013

Related U.S. Application Data

(60) Provisional application No. 61/728,492, filed on Nov. 20, 2012, provisional application No. 61/753,998, filed on Jan. 18, 2013.

(51) Int. Cl.
| | | |
|---|---|---|
| *B29C 67/00* | (2006.01) | |
| *A61N 1/05* | (2006.01) | |
| *B33Y 10/00* | (2015.01) | |
| *A61B 17/11* | (2006.01) | |

(52) U.S. Cl.
CPC ....... *B29C 67/0062* (2013.01); *A61B 17/1128* (2013.01); *A61N 1/0551* (2013.01); *B33Y 10/00* (2014.12)

(58) Field of Classification Search
None
See application file for complete search history.

(56) References Cited

U.S. PATENT DOCUMENTS

| 4,575,330 | A | 3/1986 | Hull |
| 2004/0018226 | A1 | 1/2004 | Wnek et al. |
| 2009/0088828 | A1 | 4/2009 | Shalev et al. |
| 2010/0249356 | A1* | 9/2010 | Rathore ............... C08F 290/06 528/26 |
| 2012/0315225 | A1 | 12/2012 | Porbeni et al. |

FOREIGN PATENT DOCUMENTS

WO  WO 2008/088730 A2  7/2008

OTHER PUBLICATIONS

Sandoval, J. H., et al. "Nanotailoring photocrosslinkable epoxy resins with multi-walled carbon nanotubes for stereolithography layered manufacturing." Journal of materials science 42.1 (Dec. 9, 2006): 156-165.*

(Continued)

*Primary Examiner* — Benjamin Schiffman
(74) *Attorney, Agent, or Firm* — Helen S. Baca

(57) ABSTRACT

The present invention is related to methods of fabricating neural interfaces using 3D projection micro-stereolithography.

32 Claims, 8 Drawing Sheets

(56) References Cited

OTHER PUBLICATIONS

Arcaute, Karina, Brenda K. Mann, and Ryan B. Wicker. "Fabrication of off-the-shelf multilumen poly (ethylene glycol) nerve guidance conduits using stereolithography." Tissue Engineering Part C: Methods 17.1 (Aug. 30, 2010): 27-38.*

Hadlock, Tessa, et al. "A polymer foam conduit seeded with Schwann cells promotes guided peripheral nerve regeneration." Tissue engineering 6.2 (Jul. 9, 2004): 119-127.*

Sun C et al., "Projection micro-stereolithography using digital micro-mirror dynamic mask," Sens Actuat A: Physical. May 2005;121(1):113-20.*

Dirk SM et al., "Conductive porous scaffolds as potential neural interface materials," Report No. SAND2011-8939C, OSTI ID: 1036005, published Nov. 1, 2011, retrieved from http://www.osti.gov/scitech/servlets/purl/1036005 (23 pages).

Akin T et al., "A micromachined silicon sieve electrode for nerve regeneration applications," Transducers '91: Digest for the International Conference on Solid-State Sensors and Actuators, Jun. 24-27, 1991, pp. 128-131 (doi: 10.1109/SENSOR.1991.148818).

Akin T et al., "A micromachined silicon sieve electrode for nerve regeneration applications," IEEE Trans Biomed Eng. Apr. 1994;41(4):305-13.

U.S. Appl. No. 13/660,767, filed Oct. 25, 2012, Buerger et al.
U.S. Appl. No. 13/660,749, filed Oct. 25, 2012, Buerger et al.

Bertsch A et al., "Study of the spatial resolution of a new 3D microfabrication process: the microstereophotolithography using a dynamic mask-generator technique," J Photochem Photobiol A: Chemistry. Jul. 15, 1997;107(1-3):275-81.

Borschel GH et al., "Mechanical properties of acellular peripheral nerve," J Surg Res. Oct. 2003;114(2):133-9.

Brown XQ et al., "Evaluation of polydimethylsiloxane scaffolds with physiologically-relevant elastic moduli: interplay of substrate mechanics and surface chemistry effects on vascular smooth muscle cell response," Biomaterials. Jun. 2005;26(16):3123-9.

Cicotte KN et al., "Poly(1,3-butylene fumerate) and poly(1,3-butylene fumerate)-co-(1,3-butylene maleate) as electrospun scaffold materials," MRS Online Proceedings Library. Jan. 2009;1239:1239-VV05-02 (5 pages) (doi: 10.1557/PROC-1239-VV05-02, published online by Cambridge University Press Jan. 31, 2011).

Cicotte KN et al., "Synthesis and electrospun fiber mats of low Tg poly(propylene fumerate-co-propylene maleate)," J Appl Polymer Sci. Aug. 2010;117(4):1984-91.

Cicotte KN et al., "3D printing fumarate based polymers," MRS Online Proceedings Library. Jan. 2012;1418:171-6 (doi: 10.1557/opl.2012.103, published online by Cambridge University Press Jan. 20, 2012).

Cogan SF, "Neural stimulation and recording electrodes," Annu Rev Biomed Eng. 2008;10:275-309.

Cooke MN et al., "Use of stereolithography to manufacture critical-sized 3D biodegradable scaffolds for bone ingrowth," J Biomed Mater Res B Appl Biomater. Feb. 15, 2003;64(2):65-9.

Dirk SM et al., "Conductive electrospun and micro-stereolithographically produced porous scaffolds as potential neural interface materials," MRS Online Proceedings Library. Jan. 2012;1418:163-70 (doi: 10.1557/opl.2012.102, published online by Cambridge University Press Jan. 20, 2012).

Edell DJ, "A peripheral nerve information transducer for amputees: long-term multichannel recordings from rabbit peripheral nerves," IEEE Trans Biomed Eng. Feb. 1986;33(2):203-14.

Fisher JP et al., "Synthesis and properties of photocross-linked poly(propylene fumarate) scaffolds," J Biomater Sci Polym Ed. 2001;12(6):673-87.

Hedberg EL et al., "Controlled release of an osteogenic peptide from injectable biodegradable polymeric composites," J Control Release. Dec. 5, 2002;84(3):137-50.

Hedberg EL et al., "In vitro degradation of porous poly(propylene fumarate)/poly(DL-lactic-co-glycolic acid) composite scaffolds," Biomaterials. Jun. 2005;26(16):3215-25.

Hedberg EL et al., "In vivo degradation of porous poly(propylene fumarate)/poly(DL-lactic-co-glycolic acid) composite scaffolds," Biomaterials. Jun. 2005;26(16):4616-23.

Hedberg-Dirk EL et al., "Esters of maleic anhydride as both a new and old material for tissue engineering," MRS Online Proceedings Library. Jan. 2009;1235:1235-RR06-08 (6 pages) (doi: 10.1557/PROC-1235-RR06-08, published online by Cambridge University Press Jan. 31, 2011).

Hsu YY et al., "Effect of polymer foam morphology and density on kinetics of in vitro controlled release of isoniazid from compressed foam matrices," J Biomed Mater Res. Apr. 1997;35(1):107-16.

Kasper FK et al., "Synthesis of poly(propylene fumarate)," Nat Protoc. 2009;4(4):518-25 (20 pages).

Kim YB et al., "Electrospinning of poly(dimethyl siloxane) by sol-gel method," J Appl Polymer Sci. Dec. 2009;114(6):3870-4.

Kovacs GT et al., "Regeneration microelectrode array for peripheral nerve recording and stimulation," IEEE Trans Biomed Eng. Sep. 1992;39(9):893-902.

Kwan MK et al., "Strain, stress and stretch of peripheral nerve. Rabbit experiments in vitro and in vivo," Acta Orthop Scand. Jun. 1992;63(3):267-72.

Lacour SP et al., "Long micro-channel electrode arrays: a novel type of regenerative peripheral nerve interface," IEEE Trans Neural Syst Rehabil Eng. Oct. 2009;17(5):454-60.

Mannard A et al., Regeneration electrode units: implants for recording from single peripheral nerve fibers in freely moving animals, Science. Feb. 8, 1974;183(4124):547-9.

Mensinger AF et al., "Chronic recording of regenerating VIIIth nerve axons with a sieve electrode," J Neurophysiol. Jan. 2000;83(1):611-5.

Marquardt LM et al., "Engineering peripheral nerve repair," Curr Opin Biotechnol. Oct. 2013;24(5):887-92.

Muskin JM et al., "Three-dimensional printing using a photoinitiated polymer," J Chem Educ. May 2010;87(5): 512-4.

Navarro X et al., "A critical review of interfaces with the peripheral nervous system for the control of neuroprostheses and hybrid bionic systems," J Peripher Nerv Syst. Sep. 2005;10(3):229-58.

Navarro X et al., "Peripheral nerve regeneration through microelectrode arrays based on silicon technology," Restor Neurol Neurosci. Jan. 1, 1996;9(3):151-60.

Normann RA, "Technology insight: future neuroprosthetic therapies for disorders of the nervous system," Nat Clin Pract Neurol. Aug. 2007;3(8):444-52.

Panseri S et al., "Electrospun micro- and nanofiber tubes for functional nervous regeneration in sciatic nerve transections," BMC Biotechnol. Apr. 11, 2008;8:39 (12 pages).

Polasek KH et al., "Intraoperative evaluation of the spiral nerve cuff electrode on the femoral nerve trunk," J Neural Eng. Dec. 2009;6(6):066005 (12 pages).

Rutten WL, "Selective electrical interfaces with the nervous system," Annu Rev Biomed Eng. 2002;4:407-52.

Rydevik BL et al., "An in vitro mechanical and histological study of acute stretching on rabbit tibial nerve," J Orthop Res. Sep. 1990;8(5):694-701.

Zhao Q et al., "Rat sciatic nerve regeneration through a micromachined silicon chip," Biomaterials. Jan. 1997;18(1):75-80.

\* cited by examiner

SEQUENCE LISTING

<160> NUMBER OF SEQ ID NOS: 2

<210> SEQ ID NO 1
<211> LENGTH: 5
<212> TYPE: PRT
<213> ORGANISM: Artificial Sequence
<220> FEATURE:
<223> OTHER INFORMATION: Synthetic peptide

<400> SEQUENCE: 1

Ile Lys Val Ala Val
1               5

<210> SEQ ID NO 2

```
<211> LENGTH: 5
<212> TYPE: PRT
<213> ORGANISM: Artificial Sequence
<220> FEATURE:
<223> OTHER INFORMATION: Synthetic peptide

<400> SEQUENCE: 2

Tyr Ile Gly Ser Arg
1               5
```

FABRICATION OF NEURAL INTERFACES USING 3D PROJECTION MICRO-STEREOLITHOGRAPHY

CROSS-REFERENCE TO RELATED APPLICATIONS

This application claims the benefit of U.S. Provisional Application No. 61/728,492, filed Nov. 20, 2012, and 61/753,998, filed Jan. 18, 2013. Each of these applications is incorporated by reference herein in its entirety.

STATEMENT OF GOVERNMENT INTEREST

This invention was made with Government support under contract no. DE-AC04-94AL85000 awarded by the U.S. Department of Energy to Sandia Corporation. The Government has certain rights in the invention.

FIELD OF THE INVENTION

The present invention relates to peripheral neural interfaces and, in particular, to a method to fabricate neural interfaces using 3D projection micro-stereolithography.

BACKGROUND OF THE INVENTION

Peripheral neural interfaces are intended to facilitate the exchange of information between the nervous system and electrical circuits that can be used to control sensorimotor prosthetic devices, to restore lost function due to nerve damage, and to improve human understanding of the fundamental mechanisms of nervous system operation. This exchange of information can be bidirectional, meaning that interfaces are capable of both recording and stimulating neural activity. While neural interface applications vary widely, it is generally desirable for the devices to provide a high degree of selectivity (i.e., to independently address large numbers of very small bundles of axons at geometries that approach the single micron scale) and to stay in place for long periods of time, up to many years if possible. Like other tissue interfaces and scaffolds, the physical properties of neural interfaces must be carefully tailored to provide the desired function while maintaining the health of the surrounding tissue system. Electrical properties must be tuned to enable the interface to reliably generate and/or sense the action potentials that travel in neurons. Recording electrodes are characterized primarily by their site impedance measured at the 1 kHz characteristic frequency, which ranges from approximately 50 k$\Omega$ to 1 M$\Omega$. Neural stimulation requires safe reversible charge injection, typically at levels of tens of microamps for several milliseconds. Biphasic charge pulses are used to balance the total potential at the electrode-tissue interface, avoiding oxidation and protecting both the electrode and the surrounding tissue. Stimulating and recording microelectrodes typically range from tens of microns to several hundred microns in diameter, while extraneural macroelectrodes are generally larger. To maintain the quality of electrical connection required, neural interfaces intended for chronic use must also be highly biocompatible and must develop a healthy and intimate coupling to the nerve tissue. Therefore, surface biocompatibility, structural biocompatibility—including the minimization of forces applied to the nerve as it grows and moves—and conductivity of the nerve/device interface are required for a good neural interface.

One of the more promising neural interfaces that may enable a high degree of interconnectivity is the regenerative or sieve electrode type. Regenerative electrodes require the nerve to be transected and to re-grow through an artificial interface, ultimately reconnecting with the original or alternative tissue target. The regenerative electrode presents an opportunity to establish a permanent, integrated contact between the interface and the nerve. While highly invasive, this approach makes sense in cases where the nerve is already severed or in cases, such as amputation, where the efferent and afferent receptors that the nerve addresses are missing.

However, implementing a highly selective, healthy regenerative interface has presented a number of challenges. See A. Mannard et al., *Science* 183(4124), 547 (1974); D. J. Edell, *IEEE Trans. Biomed. Eng.* BME-33(2), 203 (1986); G. T. A. Kovacs et al., *IEEE Trans. Biomed. Eng.* 39(9), 893 (1992); T. Akin et al., *IEEE Trans. Biomed. Eng.* 41(4), 305 (1994); Q. Zhao et al., *Biomaterials* 18, 75 (1997); and A. F. Mensinger et al., *J. Neurophys.* 83, 611 (2000). In general, axons regenerate in greater numbers, to greater length, and with greater health through larger holes. See Q. Zhao et al., *Biomaterials* 18, 75 (1997); X. Navarro et al., *Restorative Neurology and Neuroscience* 9(3), 151 (1996); and S. P. Lacour et al., *IEEE Trans. Neur. Sys. Rehab. Eng.* 17(5), 454 (2009). However, larger holes decrease selectivity, creating a fundamental tradeoff between selectivity and quality of regeneration. Moreover, axons are sensitive to physical loading on the implant both during and after regrowth, and such loadings can cause high rates of axonal degeneration. See D. J. Edell, *IEEE Trans. Biomed. Eng.* BME-33(2), 203 (1986). A successful regenerative implant that could be seriously considered for chronic use in humans would need to withstand loading due to patient movement both during and after regeneration, and allow axons to grow without significant constriction.

Several approaches to interfacing between electronics and nerves have been evaluated previously and some have shown success including penetrating electrodes, sieve electrodes, and cuff electrodes. See A. Normann Richard, *Nat. Clin. Pract. Neurol.* 3(8), 444 (2007); W. L. C. Rutten, *Annu. Rev. Biomed. Eng.* 4, 407 (2002); K. H. Polasek et al., *J. Neural Eng.* 6(6), 066005 (2009). The elastic moduli of these state-of-the-art interface materials are orders of magnitudes higher than the modulus of the peripheral nerves which is around 0.45 MPa. See B. L. Rydevik et al., *J. Orthop. Res.* 8(5), 694-701 (1990). The compliance mismatch between the implant and the natural tissue creates stresses at the interfaces, impacting interface longevity and nerve health.

Common materials used for neural interfaces have included stainless steel, tungsten, platinum, platinum-iridium alloys, iridium oxide, titanium nitride, and PEDOT. See S. F. Cogan, *Annu. Rev. Biomed. Eng.* 10, 275 (2008). Most common materials that are highly electrically conductive, notably metals, are characterized by also having a large modulus of elasticity, low yield strain, and high surface hardness, meaning that they require large applied forces to deform significantly at either a surface or bulk level, and that even small deformations are permanent. Structures that include such materials (e.g. wires) can be made somewhat flexible by reducing physical dimensions. However, at the scale of peripheral nerves it becomes impractical to achieve additional flexibility by shrinking rigid conductive structures.

Therefore, a need remains for a regenerative neural interface and a method to fabricate the same that can provide significantly more mechanical flexibility at the interface to the nerve to accommodate both normal movement and natural axonal regrowth. In particular, a need remains for neural interfaces that are compatible with the mechanical properties of nerve tissue (i.e., generally have low elastic modulus, large yield strain, and low surface hardness) and simultaneously achieve high, selective and controllable electrical conductivity.

SUMMARY OF THE INVENTION

The present invention is directed to a method to fabricate a neural interface, comprising coating a photo-curable polymer resin on a substrate, displaying an image of regular pores onto the polymer resin-coated substrate using projection micro-stereolithography, and developing the imaged polymer-resin coated substrate to form a porous polymer mat having an array of pores formed therein. The polymer resin further comprises conductive particles, thereby forming a porous polymer composite mat. For example, the conductive particles comprise metal nanoparticles, metal microparticles, carbon black, graphene, or carbon nanotubes. The mass loading of the conductive particles can be between 0.5% and 70% by volume. The polymer composite mat can comprise an electrically conductive region comprising the conductive particle-loaded polymer proximate each pore and an insulating region between adjacent pores. The conductive particles are preferably elongated. The developed polymer can have a Young's modulus of the developed polymer is between 10 and 1000 kPa. The pores can have a pore size of greater than 10 μm and less than 500 μm. The thickness of porous polymer mat can be less than 300 μm. The polymer resin comprises a silicone, such as polydimethylsiloxane; a polyolefin, such as poly(butadiene); an unsaturated polyester, such as poly(butylenefumarate); a polyurethane (PU); a polyimide (PI); a polyethylene glycol (PEG), including PEG copolymers; or a ring opening metathesis polymerization (ROMP) formed polymer, such as norbornene, or a copolymer thereof. The silicone can comprise at least one photo-crosslinkable reactive group, such as an acrylate, methacrylate, maleimide, allyl, or vinyl group. For example, the photo-curable polymer resin can comprise methacryloxypropyl-terminated polydimethylsiloxane and photoinitiator bisacyl phosphine oxide.

In one aspect, the invention features a method of fabricating a neural interface, including coating a photo-curable polymer resin on a substrate, displaying an image including regular pores onto the polymer resin-coated substrate using projection micro-stereolithography, and developing the imaged polymer-resin coated substrate to form a porous polymer (e.g., a porous polymer mat) having an array of pores formed therein. In some embodiments, the image includes regular pores, where each pore has about the same dimension. In other embodiments, the image includes one or more arrays of regular pores. In further embodiments, each array includes pores having about the same dimension. In other embodiments, each array includes pores having different dimensions (e.g., diameter, length, width, pitch, etc.).

In some embodiments, the polymer resin further includes a conductive particle (e.g., a metal nanoparticle, a metal microparticle, carbon black, graphene, or a carbon nanotube) or a precursor thereof (e.g., a photoreducible graphene oxide or a metal salt, such as a metal salt that can be thermally reduced, such as with silver nitrate). In particular embodiments, the mass loading of the conductive particle or precursor thereof is from about 0.5% to about 70% by volume. In other embodiments, the mass loading of the conductive particle or precursor thereof is from about 0.5% (w/w) to about 70% (w/w) (e.g., from 0.5% to 1%, 0.5% to 5%, 0.5% to 10%, 0.5% to 20%, 0.5% to 30%, 0.5% to 40%, 0.5% to 50%, 0.5% to 60%, 1% to 5%, 1% to 10%, 1% to 20%, 1% to 30%, 1% to 40%, 1% to 50%, 1% to 60%, 1% to 70%, 1% 0 to 5%, 1% to 10%, 1% to 20%, 3% to 30%, 3% to 40%, 3% to 50%, 3% to 60%, 3% to 70%, 5% to 10%, 5% to 20%, 5% to 30%, 5% to 40%, 5% to 50%, 5% to 60%, 5% to 70%, 7% to 10%, 7% to 20%, 7% to 30%, 7% to 40%, 7% to 50%, 7% to 60%, 7% to 70%, 10% to 20%, 10% to 30%, 10% to 40"%, 10% to 50%, 10% to 60%, 10% to 70%, 15% to 20%, 15% to 30%, 15% to 40%, 15% to 50%, 15% to 60%, 15% to 70%, 20% to 30%, 20% to 40%, 20% to 50%, 20% to 60%, 20% to 70%, 25% to 30%, 25% to 40%, 25% to 50%, 25% to 60%, 25% to 70%, 30% to 40%, 30% to 50%, 30% to 60%, 30% to 70%, 35% to 40%, 35% to 50%, 35% to 60%, 35% to 70%, 40% to 50%, 40% to 60%, 40% to 70%, 45% to 50%, 45% to 60%, 45% to 70%, 50% to 60%, 50% to 70%, 55% to 60%, 55% to 70%, 60% to 70%, or 65% to 70%, where each of these percentage ranges can be for percentage by volume or percentage by (w/w)). In other embodiments, the conductive particles are elongated (e.g., having a long characteristic dimension that is at least ten times, 15 times, 20 times, 25 times, or greater than a short characteristic dimension).

In any of the embodiments, the porous polymer mat includes a polymer composite. In some embodiments, the polymer composite includes an electrically conductive region and an insulating region between adjacent pores. In particular embodiments, the electrically conductive region includes the conductive particle-loaded or conductive particle precursor-loaded polymer proximate each pore.

In some embodiments, the porous polymer mat has a Young's modulus of between about 10 and about 1000 kPa (e.g., from 10 to 50, 10 to 100, 10 to 250, 10 to 400, 10 to 500, 10 to 600, 10 to 750, 10 to 900, 25 to 50, 25 to 100, 25 to 250, 25 to 400, 25 to 500, 25 to 600, 25 to 750, 25 to 900, 25 to 1000, 50 to 100, 50 to 250, 50 to 400, 50 to 500, 50 to 600, 50 to 750, 50 to 900, 50 to 1000, 75 to 100, 75 to 250, 75 to 400, 75 to 500, 75 to 600, 75 to 750, 75 to 900, 75 to 1000, 100 to 250, 100 to 400, 100 to 500, 100 to 600, 100 to 750, 100 to 900, 100 to 1000, 200 to 250, 200 to 400, 200 to 500, 200 to 600, 200 to 750, 200 to 900, 200 to 1000, 300 to 400, 300 to 500, 300 to 600, 300 to 750, 300 to 900, 300 to 1000, 350 to 400, 350 to 500, 350 to 600, 350 to 750, 350 to 900, 350 to 1000, 400 to 500, 400 to 600, 400 to 750, 400 to 900, 400 to 1000, 450 to 500, 450 to 600, 450 to 750, 450 to 900, 450 to 1000, 500 to 600, 500 to 750, 500 to 900, 500 to 1000, 550 to 600, 550 to 750, 550 to 900, 550 to 1000, 600 to 750, 600 to 900, 600 to 1000, 650 to 750, 650 to 900, 650 to 1000, 700 to 750, 700 to 900, 700 to 1000, 750 to 900, 750 to 1000, 800 to 900, 800 to 1000, 850 to 1000, 900 to 1000, or 950 to 1000 kPa).

In some embodiments, the array of pores has a pore size of from about 10 μm to about 900 μm (e.g., 10 to 25, 10 to 50, 10 to 100, 10 to 200, 10 to 300, 10 to 400, 10 to 500, 10 to 600, 10 to 700, 10 to 800, 10 to 900, 10 to 25, 25 to 50, 25 to 100, 25 to 200, 25 to 300, 25 to 400, 25 to 500, 25 to 600, 25 to 700, 25 to 800, 25 to 900, 50 to 100, 50 to 200, 50 to 300, 50 to 400, 50 to 500, 50 to 600, 50 to 700, 50 to 800, 50 to 900, 75 to 100, 75 to 200, 75 to 300, 75 to 400, 75 to 500, 75 to 600, 75 to 700, 75 to 800, 75 to 900, 100 to 200, 100 to 300, 100 to 400, 100 to 500, 100 to 600, 100 to 700, 100 to 800, 100 to 900, 200 to 300, 200 to 400, 200 to 500, 200 to 600, 200 to 700, 200 to 800, 200 to 900, 250 to 300, 250 to 400, 250 to 500, 250 to 600, 250 to 700, 250 to 800, 250 to 900, 300 to 400, 300 to 500, 300 to 600, 300 to 700, 300 to 800, 300 to 900, 400 to 500, 400 to 600, 400 to 700, 400 to 800, 400 to 900, 450 to 500, 450 to 600, 450 to 700, 450 to 800, 450 to 900, 500 to 600, 500 to 700, 500 to 800, 500 to 900, 600 to 700, 600 to 800, 600 to 900, 700 to 800, 700 to 900, or 800 to 900 µm).

In further embodiments, the array includes a plurality of arrangements, where each arrangement includes a plurality of pores. In particular embodiments, each pore in each arrangement has the same size. In other embodiments, each pore in each arrangement has a different size.

In some embodiments, the porous polymer mat has a thickness of less than about 300 µm (e.g., from about 5 µm to about 300 µm, such as from 5 to 10, 5 to 25, 5 to 50, 5 to 75, 5 to 100, 5 to 150, 5 to 200, 5 to 250, 10 to 25, 10 to 50, 10 to 75, 10 to 100, 10 to 150, 10 to 200, 10 to 250, 10 to 300, 20 to 25, 20 to 50, 20 to 75, 20 to 100, 20 to 150, 20 to 200, 20 to 250, 20 to 300, 30 to 50, 30 to 75, 30 to 100, 30 to 150, 30 to 200, 30 to 250, 30 to 300, 50 to 75, 50 to 100, 50 to 150, 50 to 200, 50 to 250, 50 to 300, 60 to 75, 60 to 100, 60 to 150, 60 to 200, 60 to 250, 60 to 300, 70 to 75, 70 to 100, 70 to 150, 70 to 200, 70 to 250, 70 to 300, 80 to 100, 80 to 150, 80 to 200, 80 to 250, 80 to 300, 90 to 100, 90 to 150, 90 to 200, 90 to 250, 90 to 300, 100 to 150, 100 to 200, 100 to 250, 100 to 300, 125 to 150, 125 to 200, 125 to 250, 125 to 300, 150 to 200, 150 to 250, 150 to 300, 200 to 250, 200 to 300, 250 to 300, or 275 to 300 µm).

In some embodiments, the polymer resin includes a silicone (e.g., silanol-terminated polydimethylsiloxane or methacryloxypropyl-terminated polydimethylsiloxane), a polyolefin, a polyester (e.g., a polybutylene fumarate), a polyurethane, a polyimide, a polyethylene glycol (PEG) including PEG copolymers, or a ring opening metathesis polymerization formed polymer, as well as any copolymer thereof (e.g., any polymer or copolymer described herein).

In other embodiments, the polymer resin includes at least one photo-crosslinkable reactive group (e.g., an acrylate, methacrylate, maleimide, allyl, or vinyl group). In further embodiments, the polymer resin is a silicone including at least one photo-crosslinkable reactive group.

In some embodiments, the polymer resin further includes a photoinitiator (e.g., a bisacyl phosphine oxide (BAPO) such as bis(2,4,6-trimethylbenzoyl)phenylphosphine oxide, 2-[bis(2,4,6-trimethylbenzoyl)phosphoryl]acetic acid (BAPO-AA), bis(2,4,6-trimethylbenzoyl)-{[2-(2-methoxyethoxy)ethoxy]ethyl}phosphine oxide (BAPO-PEG, water-soluble), bis(2,4,6-trimethylbenzoyl)-[3-tri(methoxysilyl)propyl]phosphine oxide (BAPO-TMESI), and bis(2,4,6-trimethylbenzoyl)-(rac-5norbornen-2-butyl)phosphine oxide (BAPO-NOR), phthanoyl-bis(diphenylphosphine oxide) (PBDPO), tetrafluoroterephthanoyl-bis(didiphenylphosphine oxide) (TFBDPO), bis(2,6-dimethoxybenzoyl)-2,4,4-trimethyl-pentylphosphine oxide, or bis(2,6-dichlorobenzoyl)-(4-propylphenyl)-phosphine oxide (BCPO); or monoacylphosphine oxide (MAPO), such as 7,7-dimethyl-2,3-dioxobicyclo[2.2.1]heptane-1-carbonyl-diphenylphosphine oxide (DOHC-DPPO=CQ-APO), benzoyl-diphenylphosphine oxide (BDPO), 2,4,6-trimethylbenzoylmethoxyphenylphosphine oxide (TMMPO), 2,4,6-trimethylbenzoyl diphenylphosphine oxide (TMDPO), 2,6-difluorobenzoyl-diphenylphosphine oxide (DFDPO), or (1-naphthoyl) diphenylphosphine oxide (NDPO)).

In particular embodiments, the polymer resin includes at least one photo-crosslinkable reactive group (e.g., an acrylate, methacrylate, maleimide, allyl, or vinyl group) and at least one photoinitiator (e.g., a BAPO or a MAPO, including any described herein).

In some embodiments, the porous polymer mat further includes one or more therapeutic agents (e.g., a neurotrophin, a growth factor, a cytokine, a chemokine, a lymphokine, a cell, a protein, a peptide, a drug, an axonal guidance protein, an extracellular matrix (ECM) molecule, or a morphogen, or any agent described herein). In further embodiments, the porous polymer mat includes multiple layers (e.g., as in a multilayered porous polymer mat).

In further embodiments, the porous polymer mat further includes two or more therapeutic agents, where each therapeutic agent is different (e.g., one or more neurotrophins in combination with one or more ECM molecules).

In some embodiments, the one or more therapeutic agents are encapsulated in one or more particles (e.g., nanoparticles or microparticles) or fibers (e.g., nanofibers or microfibers).

In some embodiments, the photo-curable polymer resin includes one or more therapeutic agents. In some embodiments, the photo-curable polymer resin includes one or more affinity peptides (e.g., any described herein) including one or more photo-crosslinkable reactive groups (e.g., any described herein). In other embodiments, the photo-curable polymer resin includes one or more affinity peptides (e.g., any described herein) including one or more crosslinking agents (e.g., any described herein).

In some embodiments, the method further includes adsorbing one or more therapeutic agents on the surface of the porous polymer mat and/or within one or more pores.

In some embodiments, the method further includes incorporating (e.g., electrospinning, coating, casting, spreading, dipping, spraying, and/or using projection micro-stereolithography) a delivery vehicle (e.g., a layer, a film, a polymer matrix, or a coating) on the surface, or a portion thereof, of the porous polymer mat and/or within one or more pores of the porous polymer mat, where the delivery vehicle includes one or more therapeutic agents. In some embodiments, the delivery vehicle is degradable (e.g., biodegradable, such as by including a degradable polymer). In some embodiments, the delivery vehicle comprises a polymer or a copolymer (e.g., any described herein, including ethylene-vinyl acetate, silicone, PEG, PEG copolymers, polyethyleneimine (PEI), polyimide (PI), polyurethane (PU), polycaprolactone (PCL), PCL fumarate (PCLF), polyacrylonitrile (PAN) including PAN-methacrylate, polylysine including poly-D-lysine, poly(styrenesulfonate) (PSS), PSS-PEG copolymers, poly (2-hydroxyethyl methacrylate) (pHEMA), poly (2-hydroxyethyl methacrylate-co-methyl methacrylate) (pHEMA-MMA), a polypyrrole, polyglycolic acid (PGA), polylactic acid (PLA) including poly(L-lactide) (PLLA) and poly(D-lactide) (PDLA), PGA-PLA copolymers, as well as copolymers of any of these; a hydrogel including PEG and/or a poloxamer (e.g., a triblock copolymer including PPO and PEO, such as PEO-PPO-PEO); a natural scaffold material, such as heparin, laminin, fibronectin, agarose, alginate, chitosan, cellulose (e.g., methylcellulose or nitrocellulose), collagen, dextran, fibrin, or hyaluronan/hyaluronic acid; a conductive polymer, such as polypyrrole (PPy) or polyaniline (PANi); and combinations thereof, such as collagen-PCL, PAN-methacrylate-PEG-collagen, PPy-PLGA, PLLA-PANi, PCLF-PPy, or PPy-chitosan (e.g., in a multilayered film)).

In yet another aspect, the invention features a neural interface fabricated using any method described herein.

DEFINITIONS

As used herein, the term "about" refers to +/−10% of any recited value.

By "micro" is meant having at least one dimension that is less than 1 mm. For instance, micro-stereolithography can include projection of an image having a length, width, height, cross-sectional dimension, circumference, radius (e.g., external or internal radius), or diameter that is less than 1 mm. In another instance, micro-stereolithography can include projection of an image having a length, width, height, cross-sectional dimension, circumference, radius (e.g., external or internal radius), or diameter that is larger than 1 mm but the resulting substrate can include one or more features having a dimension that is less than 1 mm (e.g., a dimension of length, width, height, cross-sectional dimension, circumference, radius (e.g., external or internal radius), or diameter, such as pore diameter, that is less than 1 mm).

Other features and advantages of the invention will be apparent from the following description and the claims.

BRIEF DESCRIPTION OF THE DRAWINGS

The accompanying drawings, which are incorporated in and form part of the specification, illustrate the present invention and, together with the description, describe the invention. In the drawings, like elements are referred to by like numbers.

DETAILED DESCRIPTION OF THE INVENTION

The present invention is directed to a method to fabricate a neural interface through which transected nerves can grow, such that small groups of neurons come into close contact with electrode sites, each of which can be connected to electronics external to the interface. The interface can be physically structured to allow neurons to grow through them by including specific openings for the axons or fascicles to grow through. They can be mechanically and biologically compatible with nerves such that they promote neuron growth and allow close integration with biological tissue, but do not harm the nervous system. They can exhibit selective and structured conductivity to allow multiple electrically independent electrode sites and the electrical properties of the interface can be tuned to enable the bidirectional transmission of neural signals. Finally, the interface can be physically and electrically connected to external circuitry, e.g. through attached wires to each of the electrode sites.

Figure 1A:
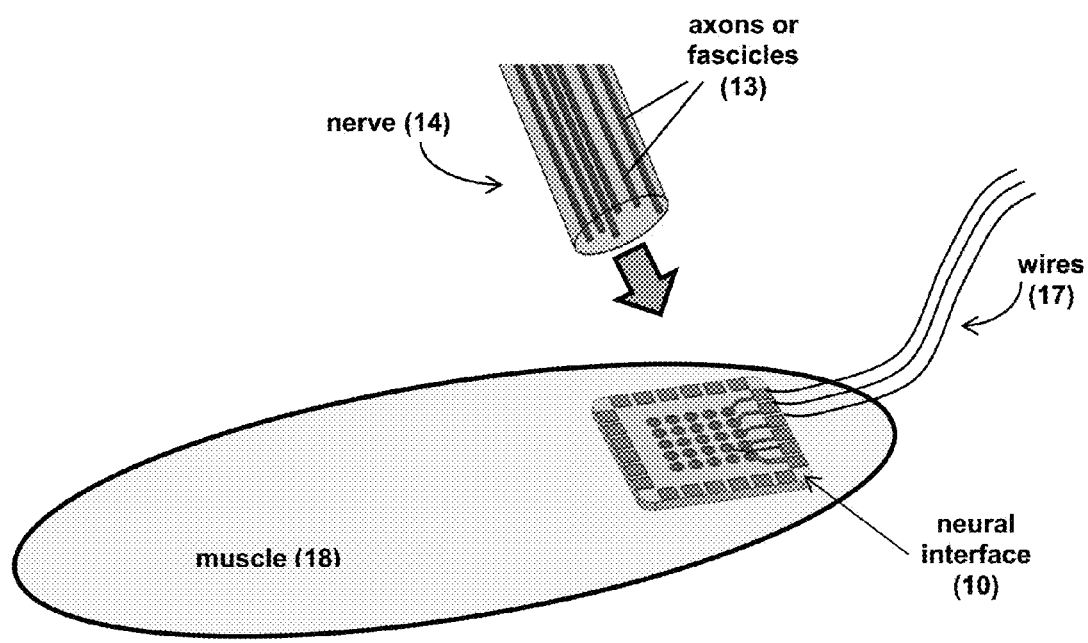
FIG. 1A-1B shows schematic illustrations of (A) a peripheral neural interface 10 with a target tissue 18 and (B) a peripheral neural interface 10 including a polymer mat 11, neural openings 12, electrode sites 15, and electrical connectors 16.
Figure 1B:
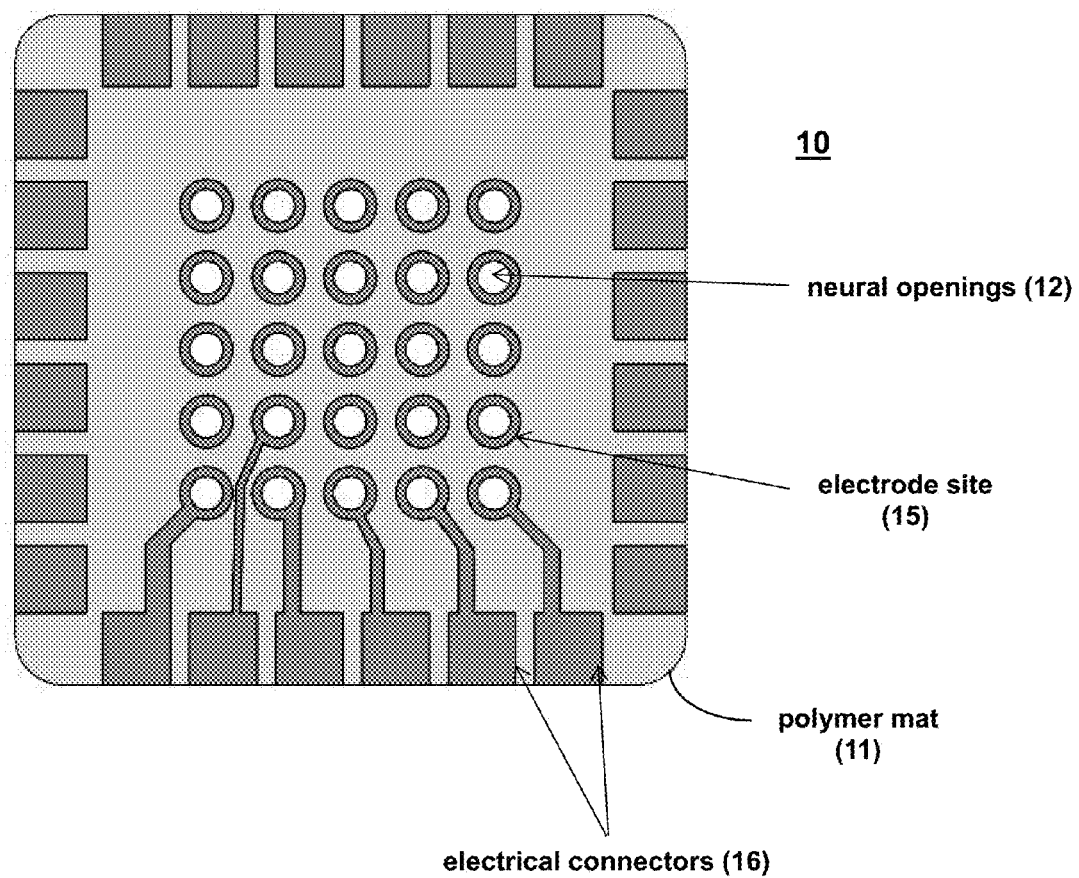

FIG. 1A is a schematic illustration of an exemplary peripheral neural interface 10. As shown in FIG. 1B, the neural interface 10 can comprise a thin, flexible selectively-conducting biocompatible polymer composite membrane or mat 11 comprising at least one opening (e.g., pore, hole, or channel) 12 for neurons, fascicles, or nerve endings 13 from a peripheral nerve 14 to grow through and where an electrically conducting electrode site 15 can be placed and connected via conductive traces and bond pads 16 within the mat via external wires 17 to electronics external to the interface. To provide selectivity of neural recording and/or stimulation, regions of the neural interface between electrode sites, between conductive traces, and between electrode and conductive traces preferably act as electrical insulators. The conductive pathways that connect electrode sites to external electronics preferably have a resistance that is one or more orders of magnitude less than the site impedance to avoid distorting signals as they are transmitted. In particular, nerve endings can grow from the proximal nerve side of the interface all the way through to the distal side, and grow into a "target" tissue, such as muscle 18, located on the distal side. The site openings can typically have cross-sectional dimension or diameter of between 10 and 500 microns, depending on the size of the axon or fascicle bundles. The interface 10 can have a thin profile (e.g., less than 300 µm thickness) and have its smallest dimension in the direction of nerve growth. The size of the interface can typically be 10-100 mm². Finally, the interface 10 can include target cells, neural growth factors or other biological compounds that encourage nerve growth. These elements can be released over time through the degradation of a polymer element, or they can be added before implantation in a host.

The neural interface can be made of composite polymer materials that are tuned via molecular formulation and the addition of small particles to have mechanical properties that are compatible with the mechanical properties of nerve tissue while also having selective electrical conductivity to enable the transmission of electrical signals to and from the neurons. The polymeric composite mat can be mechanically flexible and stretchable, so that it can move and flex with the nerve as the nerve moves and grows, minimizing the forces that the interface applies to the nerve cells. The composite mat can be made of a biocompatible polymer base material that will interact in a safe and healthy manner with surrounding cells and tissue. For example, the base polymer can comprise a polysiloxane, such as polydimethylsiloxane (PDMS); an unsaturated polyester, such as polybutylene fumarate (PBF) or polypropylene fumarate (PPF), as well as copolymers thereof (e.g., PPF/poly(propylene fumarate diacrylate) (PPF/PPF-DA)); a polyolefin, such as poly(butadiene), polybutadiene and polynorbornene copolymers; a polyurethane (PU), such as PU copolymers including PU-polycaprolactone (PL-PCL), poly(ester urethane)urea (PEUU), poly(ether ester urethane)urea (PEEUU), and thermoplastic polyurethane (TPU), such as polyester-based TPUs (mainly derived from adipic acid esters) or polyether-based TPUs (mainly based on tetrahydrofuran ethers); a polyimide; a polyethylene glycol (PEG) (or poly(ethylene oxide) (PEO), including poly(ethylene glycol fumarate) (PEGF), oligo(PEG fumarate) (OPF, a hydrogel), as well as PEG copolymers such as di- and tri-block polymers poly-caprolactone-polylactide-PEG/PEO (PCL-PLA-PEO/PEG), PCL-PEO-PCL, PCL-PEG, PLA-PEG, those including poly [(lactic acid)-co-(glycolic acid)-alt-(γ-benzyl-L-glutamic acid)] (PLGBG) such as PLGBG-PEG-PLGBG, those including poly[(lactic acid)-co-[(glycolic acid)-alt-(L-glutamic acid)] (PLGG) such as PLGG-PEG-PLGG, PEG-PCL-PEG, PEG/poly(DTE carbonate), ethylene-vinylacetate copolymer, and poly(ether ester amide)s (PEEAs) formed by polycondensation of PEG and diester-diamide to create an amphiphilic system); or a ring opening metathesis polymerization (ROMP) formed polymer, such as norbornene. It can have patterned holes, channels, or openings through which neurons can grow.

Further, the composite mat can be made electrically conductive by adding some volume fraction of conductive particles (e.g., carbon nanotubes and other particles) and/or conductive particle precursors (e.g., graphene oxide or a metal salt which can be thermally reduced, such as with silver nitrate) to the polymer base material. As the volume fraction of particulate/precursor is increased in the composite material, the composite material's physical properties transition from being approximately equal to the properties of the polymer base material to approaching the properties of the particulate/precursor. Therefore, as the volume fraction of electrically conductive particles/precursors is increased, the electrical conductivity of the composite material increases accordingly. By selecting particles/precursors with large aspect ratios (ratio of length to diameter), such as carbon nanotubes, the electrical properties of the composite can be made to transition to the properties of the particles at a lower volume fraction than the mechanical properties. Therefore polymer composites can be created with high electrical conductivity (approaching the conductivity of carbon nanotubes) and with low elastic modulus and high yield strain (approaching the mechanical properties of the base polymer). The interface can be made to be selectively conductive by locally varying the concentration of conducting particulates. That is, specific regions of the mat proximate the electrode sites can be made electrically conductive by filling with a high local volume fraction of conducting particulates, while other regions between the electrode sites can be made to be electrical insulators by using a low (or zero) local volume fraction of conducting particulates.

Electrically conductive regions or electrodes can be incorporated with the mat by any useful process. For instance, such regions can be constructed by including electrically conductive particles (e.g., carbon nanotubes) and/or by including conductive particle precursors (e.g., photoreducible metal salts or graphene oxide). Another exemplary process includes use of thin evaporated metals (e.g., gold) to form flexible conducting electrodes. Other processes can be used so long as beneficial properties of the mat are retained. Such beneficial properties include, e.g., maintaining appropriate flexibility of the implant (e.g., a modulus approximately close to a nerve, such as a peripheral nerve having a modulus of ~0.45 MPa), maintaining appropriate pore sizes (e.g., to allow infiltration and interconnection of nerves), etc.

The geometry required for optimal nerve growth can be determined from in vivo experiments. Holes or pores are preferably large enough to allow neurons to grow through, but small enough to enable interfacing with specific neurons with tight spatial resolution. Previous designs that encouraged neuron growth through holes in rigid materials (e.g., silicon) caused a significant negative impact on the health of the nerve over time. See X. Navarro et al., *J. Periph. Nerv. Sys.* 10, 229 (2005). As the neurons grew they experienced increasing pressure from the rigid orifices, ultimately resulting in neuron death. Therefore, interfaces can be made out of materials that have mechanical properties similar to those of neurons. Although there is a potentially wide variation across different types of nerves, the literature suggests that nerves behave viscoelastically and have elastic moduli of tens to hundreds of kPa (the Young's modulus for a peripheral nerve has been estimated to be 580+/−150 kPa). See M. K. Kwan et al., *Acta Orthopaedica* 63, 267 (1992); and G. H. Borschel et al., *J. Surg. Res.* 114, 133 (2003). Proper stiffness can be achieved by manipulating the material properties of the base polymer, the material properties and volume fraction of the particulates, and the structural geometry of the neural interface.

Whether used for neural stimulation or recording, impedance at the electrode is preferably low. For recording, the literature suggests electrode site impedance on the order of 100 kOhm to 1 MOhm, with lower being preferable. Site size is generally several thousand $\mu m^2$ or less. See S. Cogan, *Annu. Rev. Biomed. Eng.* 10, 275 (2008). For stimulation, the site acts as a current source, and charge injection capacity is critical and typically varies widely between several $\mu C/cm^2$ and several $mC/cm^2$. Site impedance is preferably low enough to output adequate charge without voltage exceeding the electrolysis threshold (around 1.2 V). Impedance is typically measured at the biologically-relevant frequency of 1 kHz. Conductors preferably have impedance several orders of magnitude lower than the electrode sites in order to transmit the signals without distortion. They preferably also have minimal capacitance so as not to filter signals with content into at least the tens of kHz. Ideally, cutoff frequencies can be in the hundreds of kHz or beyond.

Neural Interface Fabrication

The present invention is directed to a method to fabricate neural interfaces using three-dimensional (3D) projection micro-stereolithography (PμSL). PμSL can be used to create conductive, porous networks to meet the materials requirements for improved prosthetic neural interface devices through which transected nerves may grow, such that small groups of nerve fibers come into close contact with electrode sites. The neural interfaces can have material properties that support a healthy, functional nerve/device interface using biocompatible polymers, such as polysiloxanes (e.g., poly-dimethylsiloxane (PDMS)) or polyesters (e.g., polybutylene fumarate (PBF)), which have lower modulus of elasticity relative to previously used silicon, glass, or metal interface materials. The mechanical properties of these polymers can be made similar to those of many biological tissues. In particular, PDMS and similar polymers are widely used for biomedical and implantable applications and generally exhibit a high degree of biocompatibility. PDMS and similar polymers can also be made to be highly elastic, supporting yield strains sometimes exceeding 100%. The polymers can be loaded with some volume fraction of multi-walled carbon nanotubes (MWNTs) or other conducting particles to make the composite material electrically conductive while preserving the favorable mechanical and biocompatible properties of the base polymer. Key considerations include achieving high surface area and a porous structure, to enable integration with the nerve, biocompatibility and electrical conductivity.

Figure 2:
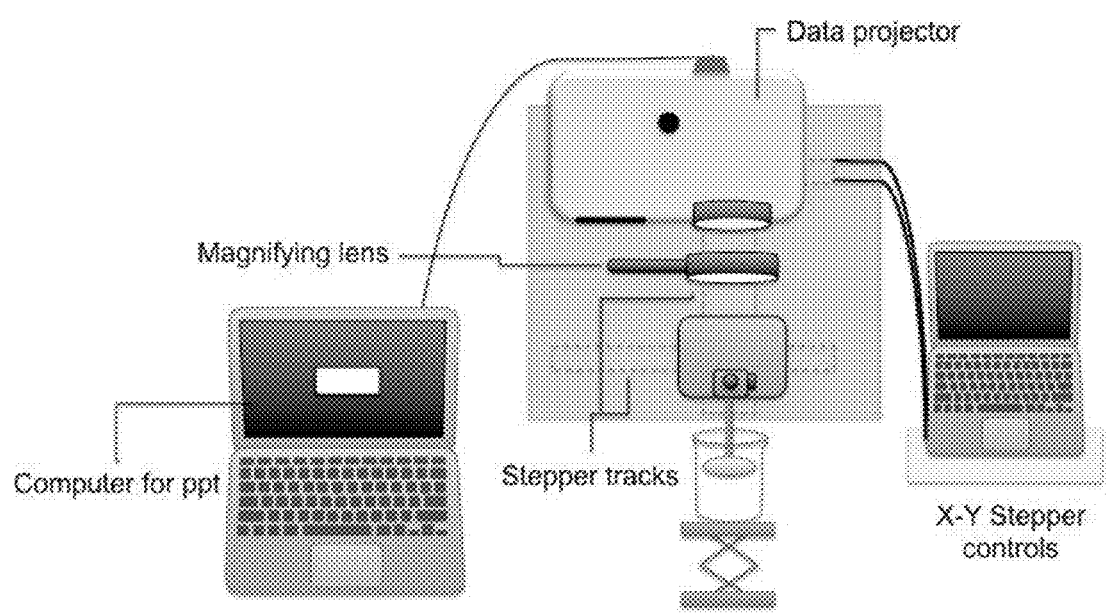
FIG. 2 is a schematic illustration of a projection micro-stereolithography apparatus that can be used to fabricate thin membranes, or mats, which contain regular arrays of pores for neural interface applications.

PµSL is a versatile, low cost process that can be used to rapidly create highly complex micro 3-D polymer structures. Because PµSL is an additive process, it is possible to make highly complex structures which are not possible via etching or other removal processes. The process can produce very high aspect ratio structures (>10) without limit in vertical direction. See J. Muskin et al., *J. Chem. Ed.* 87(5), 512 (2010); A. Bertsch et al., *J. Photochem. Photobiol. A,* 107(1-3), 275 (1997). As shown in FIG. 2, a computer and LCD projector can be used to display an image of regular pores onto a substrate having a UV or photo-curable polymer resin deposited thereon. Once a layer is polymerized, the stage drops the substrate by a predefined layer thickness, and the LCD projector displays the next image for the polymerization of the next layer on top of the preceding one. This proceeds iteratively until all the layers are complete. After exposure, the patterned polymer can be developed to reveal the regular array of pores.

Figure 3:
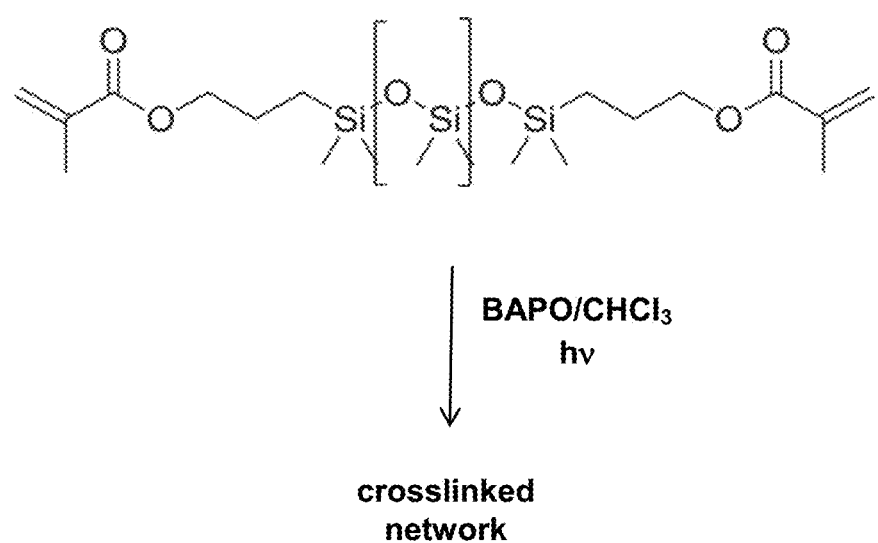
FIG. 3 shows an exemplary polymer resin comprising methacryloxypropyl terminated polydimethylsiloxane (PDMS) and the photoinitiator bisacyl phosphine oxide (BAPO) that can be used to provide an array of pores using projection micro-stereolithography.

For example, the polymer resin can comprise methacryloxypropyl-terminated polydimethylsiloxane (PDMS) and the photoinitiator bisacyl phosphine oxide (BAPO), as shown in FIG. 3. However, BAPO is not soluble in PDMS. Therefore, chloroform ($CHCl_3$) can be used to disperse the BAPO within the methacrylate-capped PDMS. Cross link density and rate can be controlled by the light intensity. The cross-linked array structure can be developed using various solvent systems, including dichloroethane, hexane, toluene and water.

As an example, a solution of phenylbis(2,4,6-trimethylbenzoyl)-phosphine oxide (0.03 g) was dissolved in 300 uL of $CHCl_3$. This solution was then added to methacryloxypropyl-terminated polydimethylsiloxane (3 g) and vortexed briefly to ensure solution homogeneity. A 1×1 inch silicon chip was placed on the stage of the printing apparatus; to this chip was added 150 µL of the PDMS/BAPO solution. The solution is allowed to self-level (~2 minutes) and then was exposed for 30 seconds. Upon exposure, the cross-linked structure was developed using various solvent systems. Once rinsed, the structure was further cross-linked via a UV source ($\lambda$=365 nm).

Figure 4A:
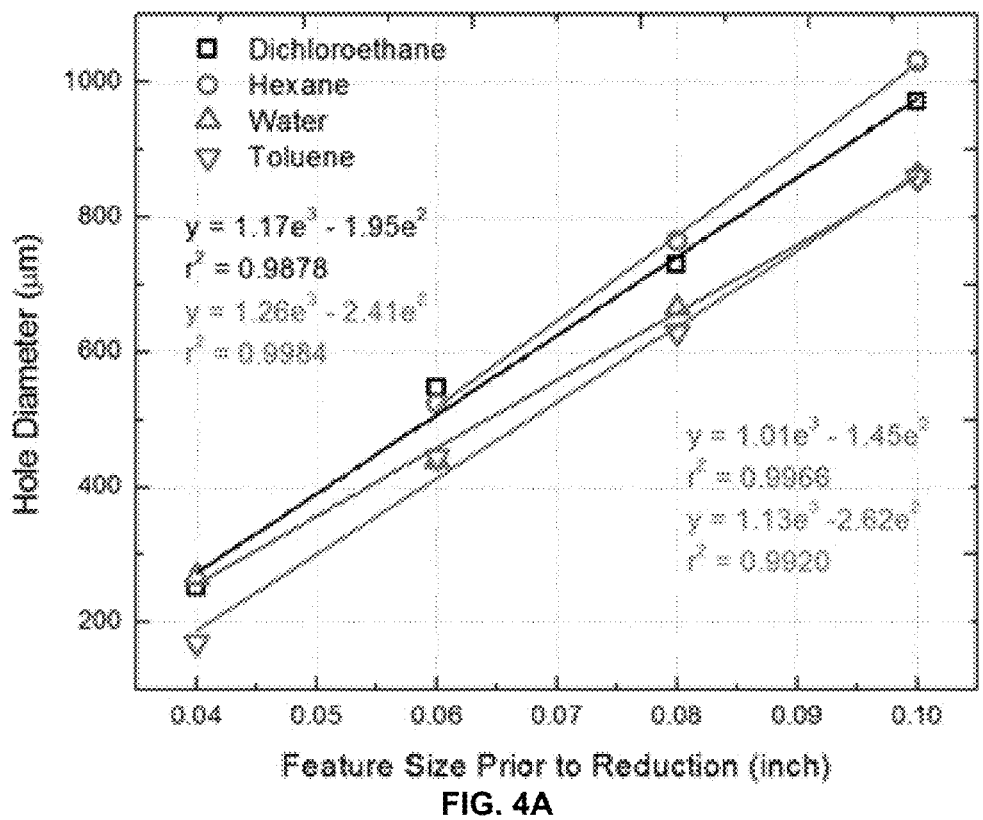
FIG. 4A-4B shows graphs of pore sizes that can be achieved by (A) using a variety of development solvents and by (B) using solvent combinations.
Figure 4B:
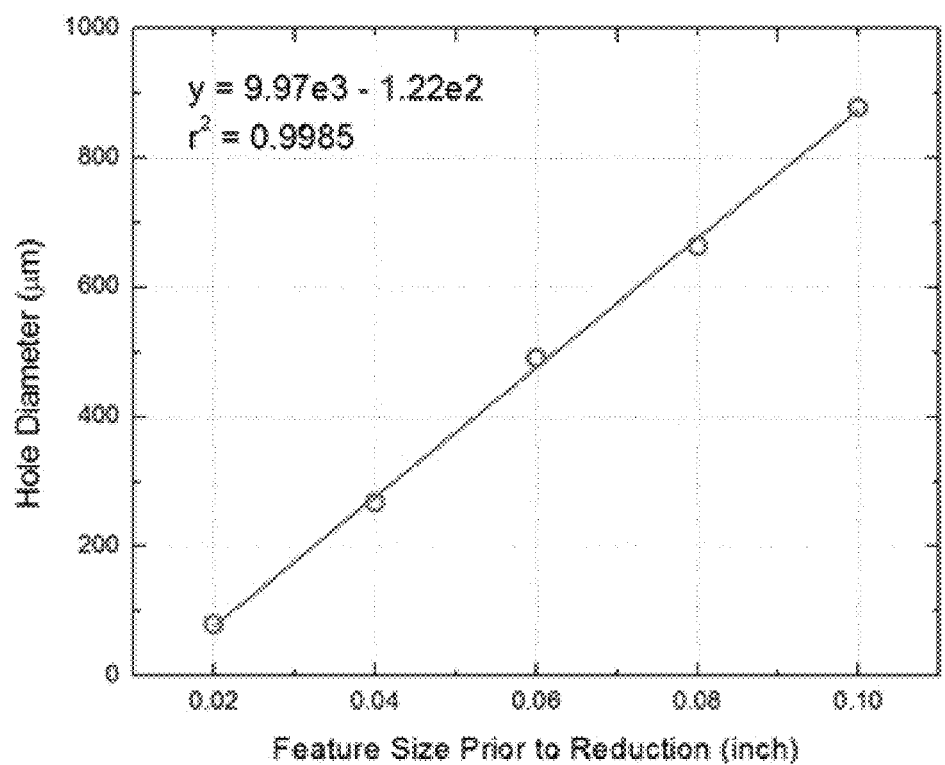

Many solvents and solvent combinations can be used to determine the ideal development conditions and feature size. In particular, the development solvent plays a key role in the final feature size, as shown in FIG. 4A. Combinations of solvents can be used as developers in order to fully develop and reveal the pores. As shown in FIG. 4B, the smallest pores can be fabricated using sequential development conditions, for example, starting with a toluene rinse followed by a water rinse. For example, a toluene/water solvent combination resulted in 79 µm diameter pores.

Figure 5A:
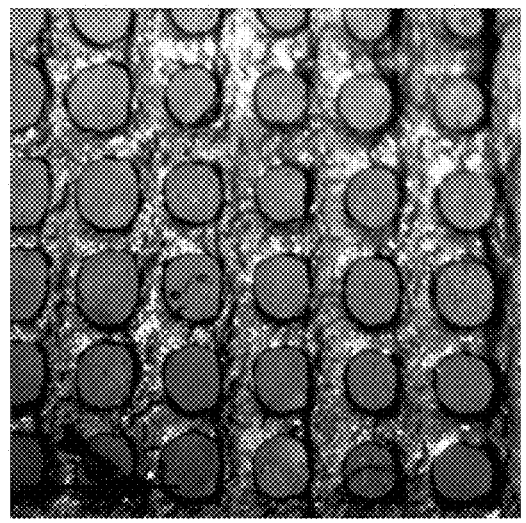
FIG. 5A-5C shows optical images of a large area patterned PDMS mat with (A) hole size of 320 µm and pitch of 570 µm, (B) hole size of 580 µm and pitch of 940 µm, and (C) hole size of 740 µm and pitch of 1000 µm.
Figure 5B:
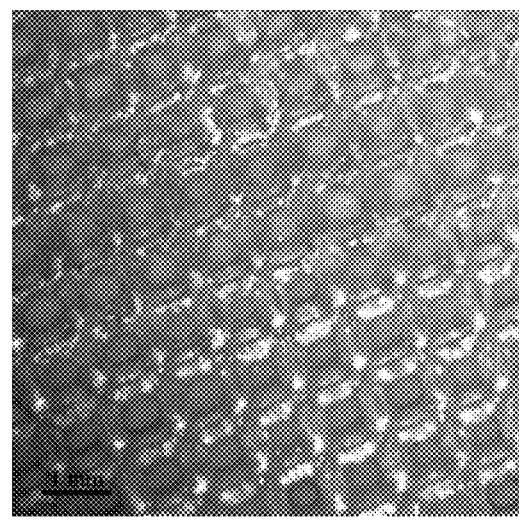
Figure 5C:
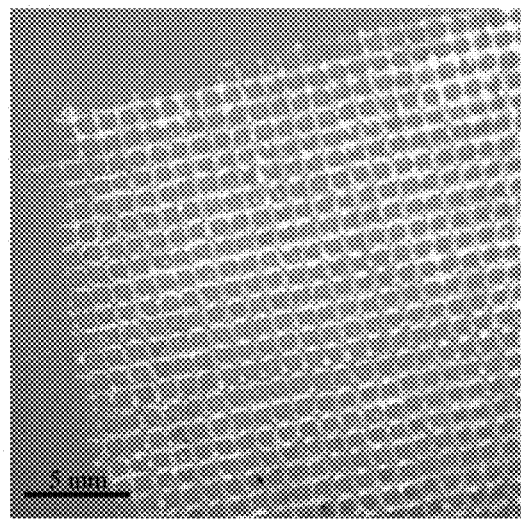

FIG. 5A is an optical image of a large area (1×1 inch) patterned PDMS mat with holes size of 320 µm and pitch of 570 µm that was developed in toluene for 5 sec. FIG. 5B is an optical image of a large area patterned PDMS mat with holes size of 580 µm and pitch of 940 µm that was developed in water for 5 sec. FIG. 5C is an optical image of a large area patterned PDMS mat with holes size of 740 µm and pitch of 1000 µm that was developed in water for 5 sec. Using these developers, the feature sizes of the holes were reduced by about 3.4 to 4.8 times.

Figure 6:
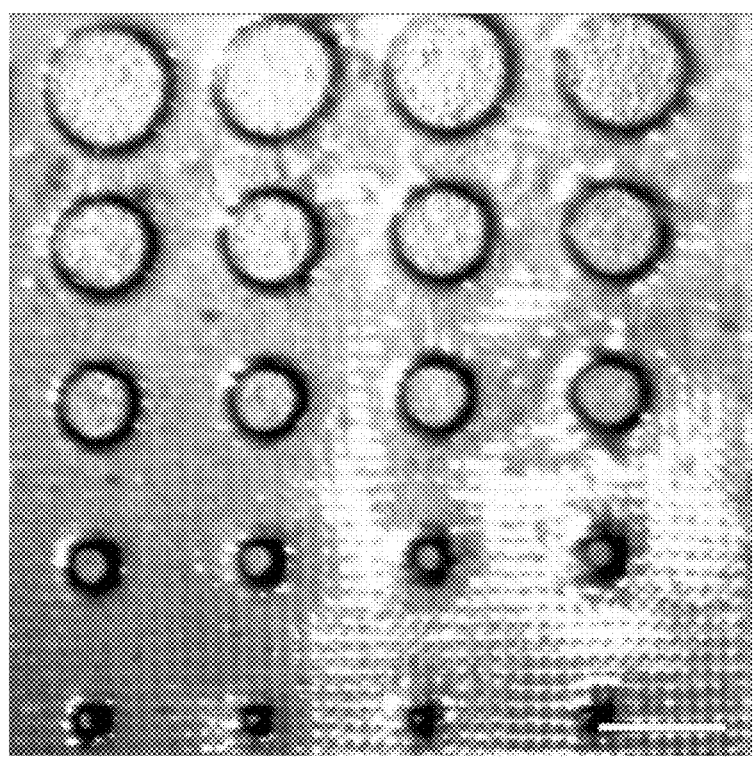
FIG. 6 shows an optical image wherein one projection mask was used to develop all feature sizes at one time.

FIG. 6 shows an optical image wherein one projection mask was used to develop all feature sizes at one time.

Figure 7:
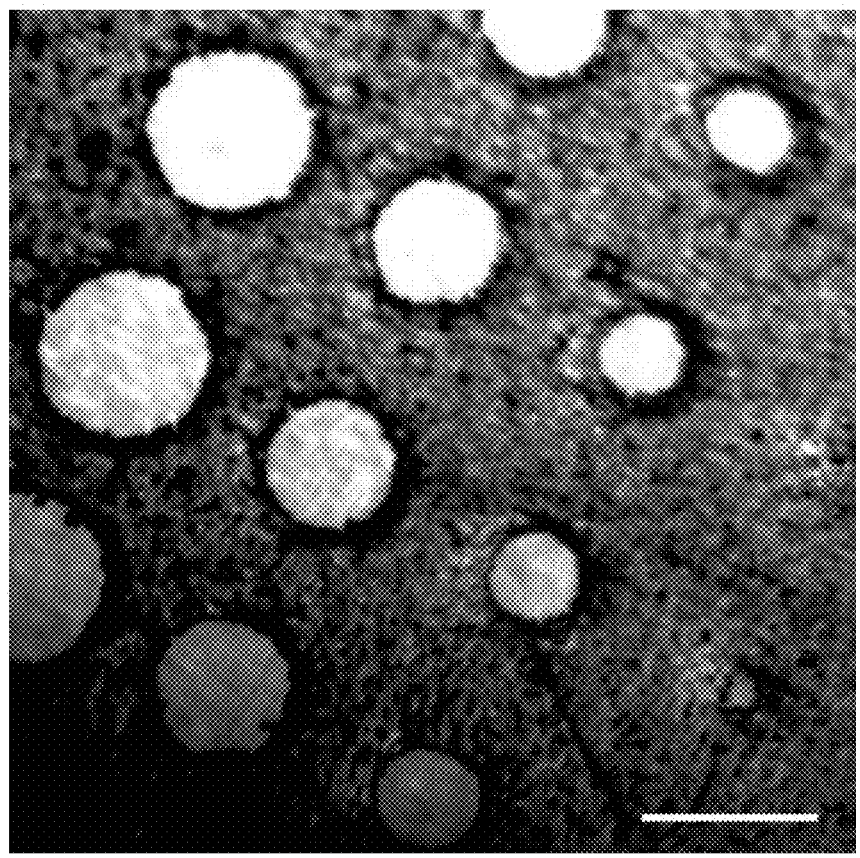
FIG. 7 is an optical image showing patterned holes fabricated in PDMS containing 10% (w/w) MWNTs. The scale bar is 1 mm.
Figure 8:
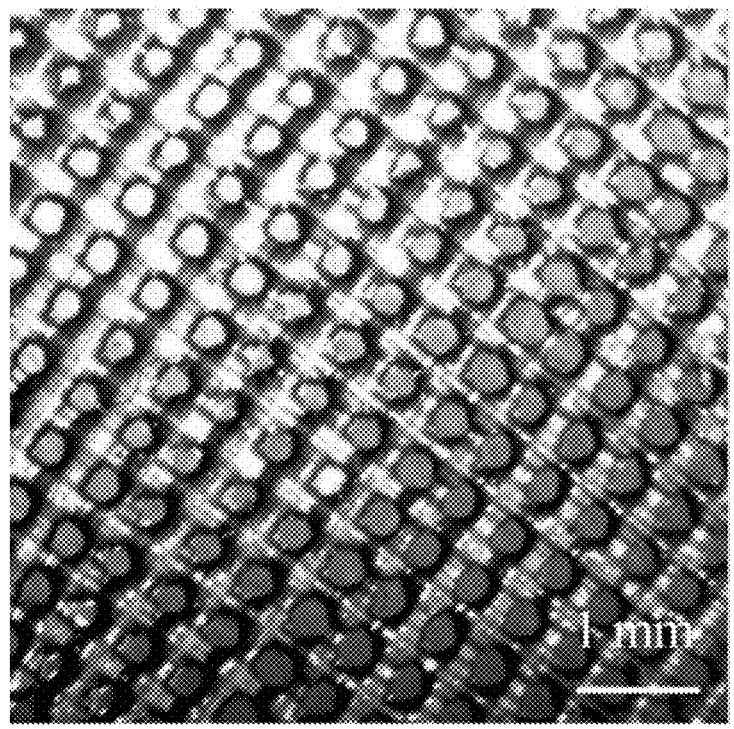
FIG. 8 is an optical image showing patterned holes fabricated in PDMS with hole sizes of about 221 µm and pitch of about 527 µm. The scale bar is 1 mm.

To provide an electrically active material interface, the PµSL technique was also used to pattern regular arrays of pores with PDMS containing multi-walled carbon nanotubes (MWNT). Projection micro-stereolithography of the MWNT loaded PDMS requires approximately two times as much exposure time to ensure patterning. The increased exposure time was due to light absorption by the MWNTs themselves, which slows photo crosslinking of the methacryloxypropyl terminated polydimethylsiloxane. FIG. 7 is an optical image of patterned holes fabricated in PDMS containing 10% (w/w) MWNTs. The features sizes of the holes shown are approximately 910 µm, 687 µm, and 458 µm. A large area (1×1 inch) array of pores in PDMS was fabricated using the PµSL technique in combination with a toluene developing solution (FIG. 8). For this array, pore diameters of 221 µm with a pitch of 527 µm were attained.

The present invention has been described as a method to fabricate neural interfaces using 3D projection lithography. It will be understood that the above description is merely illustrative of the applications of the principles of the present invention, the scope of which is to be determined by the claims viewed in light of the specification. Other variants and modifications of the invention will be apparent to those of skill in the art.

Therapeutic Agents

The neural interface and/or polymer mats of the invention can further include one or more therapeutic agents. Such therapeutic agents can be beneficial for promoting nerve regeneration and growth, reducing inflammatory responses to implantation of a neural interface, and/or minimizing scar tissue formation.

Exemplary non-limiting agents include a neurotrophin (e.g., nerve growth factor (NGF), neurotrophin-3 (NT-3), neurotrophin-4/5 (NT-4/5), a neuregulin (e.g., neuregulin 1, 2, 3, or 4), brain derived neurotrophic factor (BDNF), glial derived neurotrophic factor (GDNF), ciliary neurotrophic factor (CNTF), neurturin, artemin, persephin, glia maturation factor (GMF), or pituitary adenylate cyclase-activating polypeptide (PACAP)); a growth factor (e.g., CNTF, fibroblast growth factors (acidic and basic, aFGF and bFGF), transforming growth factor β (TGF-β), transforming growth factor α (TGF-α), GDNF, neurturin, epidermal growth factor (EGF), insulin-like growth factor (IGF), leukemia inhibitory factor (LIF), bone morphogenetic protein (BMP), or platelet-derived growth factor (PDGF)); a cytokine (e.g., an interleukin (IL), such as IL-1, IL-18, IL-2, IL-4, IL-10, IL-13, IL-6, IL-17, or IL-12; a tumor necrosis factor (TNF), such as TNF (formerly TNF-α) and lymphotoxin-alpha (formerly TNF-β); an interferon (IFN), such as IFN-α, IFN-α2a, IFN-α2b, IFN-β, IFN-β1a, IFN-γ, IFN-γ1b, and human leukocyte interferon-alpha (HuIFN-α-Le), including peglylated forms thereof); transforming growth factor β (TGF-β); erythropoietin (EPO); thrombopoietin (TPO); stem cell factor (SCF), a colony-stimulating factor (CSF, such as CSF1, CSF2, CSF3, or promegapoietin), or secreted phosphoprotein 1 (SPP1)); a chemokine, such as a CC chemokine (e.g., CCL1, monocyte chemoattractant protein-1 (CCL2/MCP-1), macrophage inflammatory protein-1α (CCL3/MIP-1α), CCL3L1, CCL3L3, macrophage inflammatory protein-1β (CCL4/MIP-1β), CCL4L1, CCL4L2, CCL5/RANTES, CCL6, CCL7, CCL8, macrophage inflammatory protein-1γ (CCL9/CCL10/MIP-1γ), eotaxin (CCL11), CCL12, CCL13, CCL14, CCL15, CCL16, CCL17, CCL18, CCL19, CCL20, CCL21, CCL22, CCL23, CCL24, CCL25, CCL26, CCL27, or CCL28), a CXC chemokine (e.g., CXCL1/KC, CXCL2, CXCL3, CXCL4, CXCL4L1, CXCL5, CXCL6, CXCL7, CXCL8, CXCL9, CXCL10, CXCL11, CXCL12, CXCL13, CXCL14, CXCL15, CXCL16, CXCL17, or LIX), a C chemokine (e.g., lymphotactin-α (XCL1) and lymphotactin-β/SCM-1 beta (XCL2)), or a $CX_3C$ chemokine (e.g., fractalkine ($CX_3CL1$)); a lymphokine, e.g., IL-2, IL-3, IL-4, IL-5, IL-6, granulocyte-macrophage colony-stimulating factor (GM-CSF), or IFN-γ; a cell (e.g., a glial cell, a Schwann cell, a neuronal cell, a neural progenitor cell, a stem cell, a bone mesenchymal stromal cell (BMSC), an immune response cell (e.g., a lymphocyte such as a T-cell or a B-cell, a macrophage, a phagocyte such as a monocyte or a macrophage or a dendritic cell, a mast cell, a platelet, a white blood cell (e.g., including a neutrophil, a basophil, an eosinophil, a lymphocyte, a natural killer cell, and a monocyte), a red blood cell, an antigen presenting cell), etc.); a protein (e.g., an antibody or an enzyme such as chondroitinase ABC or a protease); a peptide (e.g., an affinity peptide, such as RGD, IKVAV (SEQ ID NO:1), or YIGSR (SEQ ID NO:2)); a drug, such as a steroid or an anti-inflammatory agent (e.g., dexamethasone or α-melanocyte stimulating hormone (α-MSH)); an axonal guidance protein (e.g., a netrin, a slit, a semaphorin, an ephrin, or a cell adhesion molecule (CAM)); an extracellular matrix (ECM) molecule (e.g., laminin, fibronectin, tenascin, a proteoglycan (e.g., heparan sulfate, chondroitin sulfate, or keratan sulfate), a polysaccharide (e.g., hyaluronic acid), a fiber (e.g., elastin or collagen, including fibrillar (Types I-III, V, and XI), facit (Types IX, XII, and XIV), short chain (Types VIII and X), basement membrane (Type IV), or other forms (Types VI, VII, and XIII), as well as other polymers including RGD, IKVAV (SEQ ID NO:1), or YIGSR (SEQ ID NO:2) binding sites); and/or a morphogen (e.g., Wnt or Sonic Hedgehog (SHH)).

The therapeutic agent can be included in the neural interface by any useful method. For instance, during the fabrication steps, one or more therapeutic agents can be dispersed within the photo-curable polymer resin. This approach may be desired, e.g., to store the therapeutic agent within the bulk of the polymer resin and/or to promote time-delayed release of the agent, such as by degradation or surface erosion of the polymerized resin after implantation.

In another embodiment, one or more therapeutic agents can be dispersed within the solvent system used for developing the imaged substrate. For example and without limitation, such an approach may be desired if the therapeutic agent is photosensitive to the light source used in photocuring step. Using this approach, the therapeutic agent can be deposited on the surface and within the pores of the neural interface by adsorption, absorption, or a combination thereof. Optionally, the surface and pores of the neural interface are activated to promote covalent or non-covalent binding between the surface and the therapeutic agent.

In yet another embodiment, the neural interface is first formed using the PµSL method, and a subsequent functionalization step is used to include the therapeutic agent. Exemplary non-limiting functionalization steps include immersing the porous polymer mat in a solvent (e.g., water, a buffer, etc.) including the therapeutic agent; and/or directly modifying the surface of the porous polymer mat with one or more therapeutic agents optionally using a tether (e.g., a polyethylene glycol (PEG) linker, a PEO-PPO-PEO linker having poly(propylene oxide) (PPO) and poly(ethylene oxide) (PEO), and/or an alkane chain).

Another non-limiting functionalization step includes coating the porous polymer mat with a biocompatible film containing a therapeutic agent. The film can be formed from any useful material, including a polymer including ethylene-vinyl acetate, silicone, PEG, PEG copolymers, polyethyleneimine (PEI), polyimide (PI), polyurethane (PU), polycaprolactone (PCL), PCL fumarate (PCLF), polyacrylonitrile (PAN) including PAN-methacrylate, polylysine including poly-D-lysine, poly(styrenesulfonate) (PSS), PSS-PEG copolymers, poly (2-hydroxyethyl methacrylate) (pHEMA), poly (2-hydroxyethyl methacrylate-co-methyl methacrylate) (pHEMA-MMA), a polypyrrole, polyglycolic acid (PGA), polylactic acid (PLA) including poly(L-lactide) (PLLA) and poly(D-lactide) (PDLA), PGA-PLA copolymers, as well as copolymers of any of these; a hydrogel including PEG and/or a poloxamer (e.g., a triblock copolymer including PPO and PEO, such as PEO-PPO-PEO); a natural scaffold material, such as heparin, laminin, fibronectin, agarose, alginate, chitosan, cellulose (e.g., methylcellulose or nitrocellulose), collagen, dextran, fibrin, or hyaluronan/hyaluronic acid; a conductive polymer, such as polypyrrole (PPy) or polyaniline (PANi); and combinations thereof, such as collagen-PCL, PAN-methacrylate-PEG-collagen, PPy-PLGA, PLLA-PANi, PCLF-PPy, or PPy-chitosan (e.g., in a multilayered film). The biocompatible film can be formed by any useful process, including electrospinning, coating, casting, spreading, dipping, and/or spraying a solution including the therapeutic agent and the polymer/monomer forming the film layer.

Furthermore, the incorporation of one or more therapeutic agents can be optimized based on the type of agent. For instance, one or more ECM molecules (e.g., any described herein) could be incorporated into the neural interface in any useful manner. In one embodiment, the ECM molecule could be incorporated into the polymer resin solution prior to crosslinking, allowing such molecules to be physically entrapped into the polymer matrix. In particular embodiments, entrapment includes use of one or more hydrophilic polymers. In another embodiment, the ECM molecule is adsorbed onto the surface of the implant. In yet another embodiment, when the ECM molecule is a protein, such protein sequences (e.g., sequences including RGD, IKVAV (SEQ ID NO:1), or YIGSR (SEQ ID NO:2)) can be crosslinked into the polymer network by adding photoactive functional crosslinking groups to the protein sequence (e.g., adding acrylate or methacrylate groups to end(s) and/or using crosslinkable amino acid sequences, such as amino acids including a sulfhydryl group, an azide group, an diazirine group, a hydroxyl group, an amino group, or an aldehyde group). Crosslinking can optionally include use of a crosslinking agent, such as disuccinimidyl suberate (DSS), bismaleimidoethane (BMOE), bis[sulfosuccinimidyl] suberate (BS3), dicyclohexylcarbodiimide (DCC), sulfosuccinimidyl 4-(N-maleimidomethyl)cyclohexane-1-carboxylate (Sulfo-SMCC), n-unit ethyleneglycol functionalized with succinimidyl and maleimido ends (SM(PEG)n, where n is 2, 4, 6, 8, or 12), 1-ethyl-3-(3-dimethylaminopropyl)carbodiimide hydrochloride (EDC), N-hydroxysuccinimide (NHS), N-hydroxysulfosuccinimide (Sulfo-NHS), psoralen such as succinimidyl-[4-(psoralen-8-yloxy)]-butyrate (SPB), or p-maleimidophenyl isocyanate (PMPI). Although these embodiments include an ECM molecule, a skilled artisan would understand that any therapeutic agent (e.g., a drug, a growth factor, etc.) could be incorporated in any of the steps described above.

In another example, the neural interface is modified to deliver one or more therapeutic agents, such as drugs, growth factors, cytokines, chemokines, peptides, etc. or any described herein. In one embodiment, the therapeutic agent is adsorbed onto the surface of the implant. In another embodiment, the therapeutic agent is incorporated into the polymer resin solution prior to crosslinking. In this manner, the agent is physically entrapped within the polymer matrix. In particular embodiments, the resin includes one or more hydrophilic polymers. In other embodiment, the agent is entrapped within microparticles (e.g., degradable or nondegradable microparticles) that are included in the polymer solution before crosslinking. This method may be beneficial to protect the therapeutic agent from harsh conditions, as well as to tune the rate of controlled release.

In some embodiments, the agent is included in the neural interface obtained after PμSL. For instance, the agent can be included in a degradable matrix, which is further disposed within the pores of the polymer mat. In another instance, the agent can be included in a degradable layer on one or both sides of the implant, where the degradable layer includes a therapeutic agent that is optionally present in nanoparticles and/or microparticles. The degradable layer can be included in any useful manner, such as by coating, casting, spreading, dipping, and/or spraying a solution including the therapeutic agent and the polymer/monomer forming the degradable layer. In yet other embodiments, one or more degradable or non-degradable layers are included by electrospinning microfibers or nanofibers on one or both sides of implant, where the implant and/or the microfiber or nanofiber contains therapeutics for controlled release.

In other embodiments, the agent is included in the neural interface during the PμSL process. For instance, the implant can be a multilayered device formed by PμSL, where the outermost layer includes a degradable delivery vehicle (e.g., a degradable layer including one or more therapeutic agents optionally present in nanoparticles and/or microparticles). In particular embodiments, the implant include a plurality of degradable layers, where each layer includes a different combination of therapeutic agents. In other embodiments, each layer includes the same therapeutic agent having different release profiles.

For any methods and implants described herein, any of the methods described herein can be used to include multiple agents. In some embodiments, each agent can be released to have a unique release profile (i.e., temporal control). In other embodiments, each agent can be released in a manner that varies with the location of the agent (i.e., spatial control), where the location can be either within the z-dimension of the implant (e.g., along the thickness of the implant) or the x- or y-dimension of the implant (e.g., along the surface of implant provided in FIG. 1B).

For any methods and implants described herein, agents can be selected to promote nerve regeneration. For instance, the agent can be those that target different cell types involved in regeneration (e.g., one or more of nerves, stem cells, immune response cells, etc.). In other embodiments, the agent is a neurotrophin (e.g., any described herein).

The therapeutic agent can be present in any useful form. For instance, the therapeutic agent can be encapsulated in one or more particles or fibers (e.g., microparticles, microspheres, beads, nanoparticles, microfibers, and/or nanofibers), produced by one or more cells, present in one or more degradable or non-degradable films or coatings, and/or covalently or non-covalently attached to the surface of the neural implant.

For any of the approaches described herein, a skilled artisan would understand how to optimize the fabrication steps to promote particular release characteristics of the therapeutic agent. For instance, the developing step can be optimized to control the crosslinking density of the polymer, which can affect the release profile of the therapeutic agent by diffusion and/or erosion of the polymer. Crosslinking density can be controlled in many ways, such as by modifying the concentration of the polymer precursor in the polymer resin; by adjusting the concentration of the photoinitiator and/or ratio of photo-crosslinkable reactive groups to non-reactive groups; and/or by regulating the curing time of the resin or the light intensity used for stereolithography. The release profile of the therapeutic agent can be further optimized by fine-tuning the pore size within the neural interface, the loading amount of one or more therapeutic agents (optionally encapsulated within a particle, as described herein), the composition of the polymer resin, the affinity of a coating to the therapeutic agent, etc. In addition, release profiles can be controlled through selection of material and method of inclusion of the agent.

OTHER EMBODIMENTS

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are within the claims.

The invention claimed is:

1. A method of fabricating a neural interface, comprising:
coating a photo-curable polymer resin on a substrate,
displaying an image comprising regular pores onto the polymer resin-coated substrate using projection microstereolithography, thereby cross-linking the resin, and
developing the imaged polymer-resin coated substrate in the presence of a first solvent system, thereby revealing an array of pores formed within a porous polymer mat, wherein the first solvent system determines a feature size of the pores, and
wherein the developing step provides a reduction in the feature size of pores within the porous polymer mat, as compared to a feature size of the regular pores provided in the image.

2. The method of claim 1, wherein the polymer resin further comprises a conductive particle or a precursor thereof, and wherein the porous polymer mat comprises a polymer composite.

3. The method of claim 2, wherein the conductive particle comprises a metal nanoparticle, a metal microparticle, carbon black, graphene, or a carbon nanotube; or wherein the conductive particle precursor comprises a photoreducible graphene oxide or a metal salt.

4. The method of claim 2, wherein the mass loading of the conductive particle or precursor thereof is from about 0.5% to about 70% by volume.

5. The method of claim 2, wherein the polymer composite comprises an electrically conductive region and an insulating region between adjacent pores.

6. The method of claim 5, wherein the electrically conductive region comprises the conductive particle-loaded or conductive particle precursor-loaded polymer proximate each pore.

7. The method of claim 2, wherein the conductive particles are elongated.

8. The method of claim 7, wherein the elongated conductive particles have a long characteristic dimension that is at least ten times greater than a short characteristic dimension.

9. The method of claim 1, wherein the porous polymer mat has a Young's modulus of between about 10 and about 1000 kPa.

10. The method of claim 1, wherein the array of pores has a pore size of from about 10 μm to about 900 μm.

11. The method of claim 1, wherein the porous polymer mat has a thickness of less than about 300 μm.

12. The method of claim 1, wherein the polymer resin comprises a silicone, a polyolefin, a polyester, a polyurethane, a polyimide, a polyethylene glycol, or a ring opening metathesis polymerization formed polymer, or a copolymer thereof.

13. The method of claim 12, wherein the polymer resin is the polyester comprising polybutylene fumarate.

14. The method of claim 12, wherein the polymer resin is the silicone comprising silanol-terminated polydimethylsiloxane.

15. The method of claim 12, wherein the polymer resin is the silicone comprising at least one photo-crosslinkable reactive group.

16. The method of claim 15, wherein the at least one photo-crosslinkable reactive group comprises an acrylate, methacrylate, maleimide, allyl, or vinyl group.

17. The method of claim 16, wherein the silicone comprises methacryloxypropyl-terminated polydimethylsiloxane.

18. The method of claim 12, wherein the polymer resin further comprises a photoinitiator.

19. The method of claim 18, wherein the photoinitiator is a bisacyl phosphine oxide or a monoacylphosphine oxide.

20. The method of claim 18, wherein the polymer resin further comprises at least one photo-crosslinkable reactive group.

21. The method of claim 1, wherein the porous polymer mat further comprises one or more therapeutic agents.

22. The method of claim 21, wherein the therapeutic agent is selected from the group consisting of a neurotrophin, a growth factor, a cytokine, a chemokine, a lymphokine, a cell, a protein, a peptide, a drug, an axonal guidance protein, an extracellular matrix (ECM) molecule, and a morphogen.

23. The method of claim 22, wherein the porous polymer mat further comprises one or more neurotrophins and one or more ECM molecules.

24. The method of claim 21, wherein the one or more therapeutic agents are encapsulated in one or more particles or fibers.

25. The method of claim 1, wherein the photo-curable polymer resin comprises one or more therapeutic agents.

26. The method of claim 1, further comprising adsorbing one or more therapeutic agents on the surface of the porous polymer mat and/or within one or more pores.

27. The method of claim 1, further comprising incorporating a delivery vehicle on the surface, or a portion thereof, of the porous polymer mat and/or within one or more pores of the porous polymer mat, wherein the delivery vehicle comprises one or more therapeutic agents.

28. The method of claim 27, wherein the delivery vehicle comprises a degradable polymer.

29. The method of claim 27, wherein the incorporating step comprises electrospinning, coating, casting, spreading, dipping, spraying and/or using projection micro-stereolithography.

30. The method of claim 1, wherein the first solvent system comprises dichloroethane, hexane, toluene, water, or combinations thereof.

31. The method of claim 1, wherein the developing step comprises developing the imaged polymer-resin coated substrate in the presence of the first solvent system to provide a resultant substrate and then further developing the resultant substrate in the presence of a second solvent system, and wherein the first and second solvent systems are different.

32. The method of claim 1, wherein the displaying step comprises use of a light source.

\* \* \* \* \*